(12) United States Patent
Sato

(10) Patent No.: US 12,733,939 B2
(45) Date of Patent: Sep. 15, 2026

(54) OSTEOTOMY ASSISTANCE JIG, DIGITAL TEMPLATE, AND LONG BONE CORRECTIVE OSTEOTOMY

(71) Applicant: OSferionBiomaterials Corp., Tokyo (JP)

(72) Inventor: Takashi Sato, Niigata (JP)

(73) Assignee: OSferionBiomaterials Corp., Tokyo (JP)

( * ) Notice: Subject to any disclaimer, the term of this patent is extended or adjusted under 35 U.S.C. 154(b) by 133 days.

(21) Appl. No.: 18/729,976

(22) PCT Filed: Jan. 18, 2023

(86) PCT No.: PCT/JP2023/001384
§ 371 (c)(1),
(2) Date: Jul. 18, 2024

(87) PCT Pub. No.: WO2023/140292
PCT Pub. Date: Jul. 27, 2023

(65) Prior Publication Data

US 2025/0099110 A1 Mar. 27, 2025

(30) Foreign Application Priority Data

Jan. 20, 2022 (JP) ................................ 2022-007120

(51) Int. Cl.
*A61B 17/15* (2006.01)
*A61B 34/10* (2016.01)

(52) U.S. Cl.
CPC ...... *A61B 17/151* (2013.01); *A61B 2034/102* (2016.02)

(58) Field of Classification Search
CPC . A61B 17/151; A61B 2034/102; A61B 17/15; A61B 34/10; A61B 2034/105;
(Continued)

(56) References Cited

U.S. PATENT DOCUMENTS

2005/0273114 A1* 12/2005 Novak ............... A61B 17/8858 606/88

FOREIGN PATENT DOCUMENTS

JP 6941393 B1 9/2021
JP 7184406 B1 12/2022
WO WO-2007047629 A2 * 4/2007 ............ A61F 5/058

OTHER PUBLICATIONS

International Search Report from International Application No. PCT/JP2023/001384 mailed Apr. 11, 2023.

* cited by examiner

*Primary Examiner* — Tarla R Patel
(74) *Attorney, Agent, or Firm* — Shih IP Law Group, PLLC.

(57) ABSTRACT

Provided is an osteotomy assistance jig, a digital template, and long bone corrective osteotomy. This osteotomy assistance jig comprises: a first registration member that has a positioning plate serving as a placement reference, and that sets a fixed position of a distal screw bolt; and a second registration member that is connected to the first registration member at an arbitrarily defined pivot angle so as to be capable of pivoting about a pivot axis set on a bone cutting line serving as a reference for cutting, and that sets a fixed position of a proximal screw bolt, wherein the fixed positions of the distal screw bolt and the proximal screw bolt are determined on the basis of the position of the first registration member and the connection position and connection angle of the second registration member with respect to the first registration member.

17 Claims, 10 Drawing Sheets

(58) Field of Classification Search
CPC ... A61B 2090/067; A61B 17/14; A61B 17/00; A61B 90/06; A61B 90/00
See application file for complete search history.

OSTEOTOMY ASSISTANCE JIG, DIGITAL TEMPLATE, AND LONG BONE CORRECTIVE OSTEOTOMY

TECHNICAL FIELD

The present invention relates to an osteotomy assistance jig for long bone correction, a digital template for long bone correction, and a long bone corrective osteotomy.

BACKGROUND ART

In a disease called knee osteoarthritis which causes a pain due to the wear of the cartilage of the knee, it is overwhelmingly common that the cartilage on the medial side of the knee is worn out, and genu varum deformity of the lower limb is the cause thereof. In the case of a genu varum, a large load is applied to the medial side of the knee, and thus, the cartilage on the medial side is easily worn. When only the cartilage on the medial side is worn, the genu varum further develops, causing the disease to progress in a vicious cycle. One of the treatments for the knee osteoarthritis is a high tibial osteotomy (HTO). In the related art, various osteotomy jigs have been proposed in order to perform the high tibial osteotomy as in preoperative planning (for example, Patent Literature (hereinafter referred to as "PLT") 1).

The high tibial osteotomy is an operation to change from a genu varum to a genu valgum by resecting the tibial proximal end of the tibia to change the shape, where the tibia is one of the two bones in the lower limb and bears most of the load, and the tibial proximal end is close to the knee. The high tibial osteotomy can relieve a pain and suppress the progression of the disease by releasing the load on the medial side to the lateral side to reduce the burden. An osteotomy such as the high tibial osteotomy is not limited to the correction of the tibia, but is also applied to a case where a long bone such as the femur is corrected.

CITATION LIST

Patent Literature

PTL 1
Japanese Patent No. 6941393

SUMMARY OF INVENTION

Technical Problem

According to the osteotomy assistance jig disclosed in PTL 1, it is possible to accurately reproduce, during an operation, an osteotomy alignment set in preoperative planning, when a closed wedge high tibial osteotomy (hereinafter referred to as "CWHTO (Closed Wedge HTO)") is performed. The osteotomy assistance jig disclosed in PTL 1 is, however, not applicable to an open wedge high tibial osteotomy (hereinafter referred to as "OWHTO (Open Wedge HTO)"). As the high tibial osteotomy, the OWHTO is more popular than the CWHTO, and it is desired to put into practical use a jig that is applicable to the OWHTO.

An object of the present invention is to provide an osteotomy assistance jig, a digital template, and a long bone corrective osteotomy each of which is also applicable to the OWHTO and is capable of accurately reproducing, during an operation, an osteotomy alignment set in preoperative planning.

Solution to Problem

An osteotomy assistance jig according to the present invention is used to set a fixing position of a distal screw bolt and a fixing position of a proximal screw bolt, where the distal screw bolt and the proximal screw bolt are for fixing a fixing plate to a long bone after bone cutting. The osteotomy assistance jig includes: a first registration member that includes a positioning plate serving as a disposition reference, and sets the fixing position of the distal screw bolt; and a second registration member that is connected to the first registration member so as to be pivotable with respect to the first registration member at an arbitrarily pivot angle around a pivot axis set on a bone cutting line serving as a reference for cutting, and sets the fixing position of the proximal screw bolt. The fixing position of the distal screw bolt and the fixing position the proximal screw bolt are set based on a position of the first registration member, and a connection position and a connection angle of the second registration member with respect to the first registration member.

A digital template according to the present invention is a digital template in which the osteotomy assistance jig described above is modeled in a side view. The digital template to be drawn includes: registration information indicating a position and a posture of the osteotomy assistance jig; bone cutting surface information indicating a bone cutting surface associated with the osteotomy assistance jig; candidate position information on the pivot axis; fixing position information on the distal screw bolt; and fixing position information on the proximal screw bolt.

A long bone corrective osteotomy according to the present invention is performed by using the osteotomy assistance jig described above, and includes: performing preoperative planning by using the digital template described above; adjusting the connection position and the connection angle of the second registration member with respect to the first registration member according to the preoperative planning; installing the osteotomy assistance jig in a predetermined portion of the long bone according to the preoperative planning; inserting a guide pin into the fixing position of the distal screw bolt and the fixing position of the proximal screw bolt by using the osteotomy assistance jig, before cutting the long bone; performing bone cutting of the long bone; positioning the fixing plate by using the guide pin as a guide while rotating the long bone after the bone cutting; and inserting the distal screw bolt and the proximal screw bolt along the guide pin to fix the fixing plate to the long bone.

Advantageous Effects of Invention

According to the present invention, it is possible to accurately reproduce, during an operation, an osteotomy alignment set in preoperative planning, not only in the CWHTO, but also in the OWHTO.

DESCRIPTION OF EMBODIMENTS

Hereinafter, an embodiment of the present invention will be described in detail with reference to the accompanying drawings.

In the present embodiment, high tibial osteotomy assistance jig 1 (hereinafter referred to as "HTO assistance jig 1") to which an osteotomy assistance jig according to the present invention is applied will be described.

In the present specification, illustration is made by using a superior-inferior direction, a left-right direction, and an anterior-posterior direction where the anatomical position is used as a reference. Further, the side close to the median plane in the left-right direction will be referred to as "medial", the side distant from the median plane in the left-right direction will be referred to as "lateral", the side close to the body trunk in the superior-inferior direction will be referred to as "proximal", and the side distant from the body trunk in the superior-inferior direction will be referred to as "distal". Note that, the components of HTO assistance jig 1 will also be described by using the "superior-inferior direction", the "left-right direction", and the "anterior-posterior direction" where a state in which HTO assistance jig 1 is disposed in a bone cutting area is used as a reference.

Figure 1A:
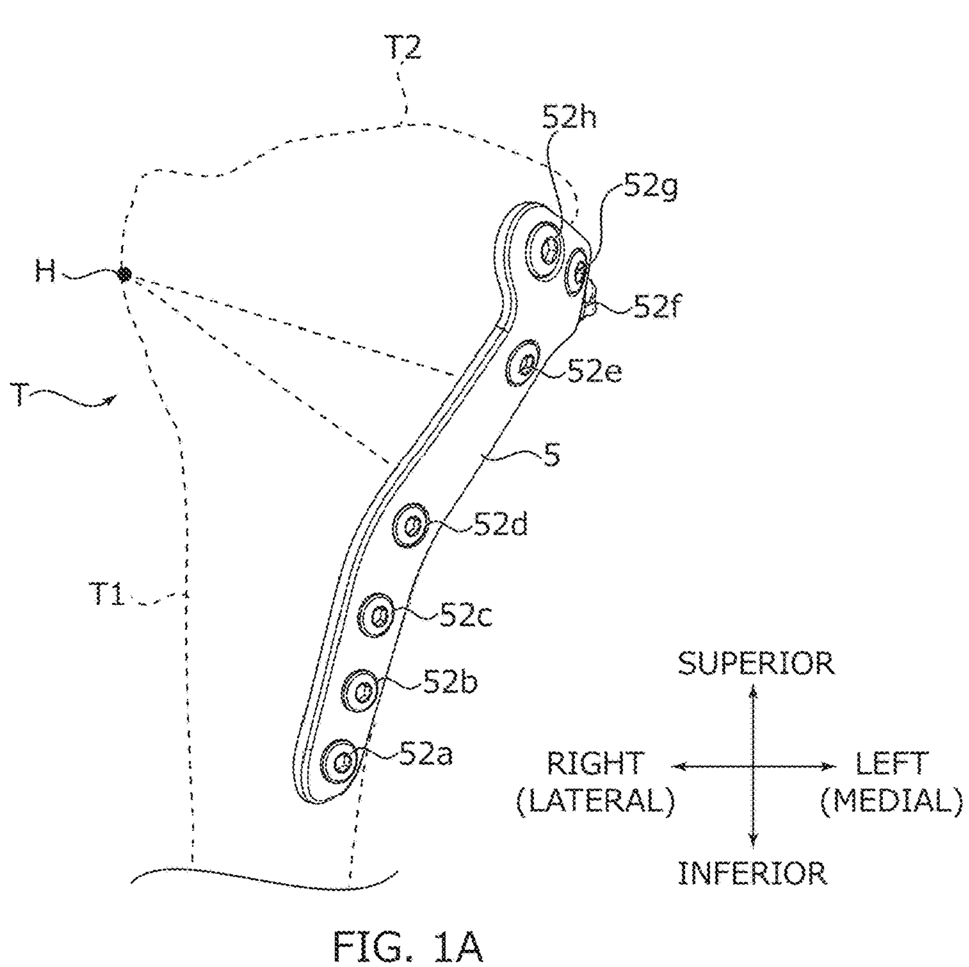
FIGS. 1A and 1B illustrate a fixing plate that is fixed to a bone cutting area of the tibia.
Figure 1B:
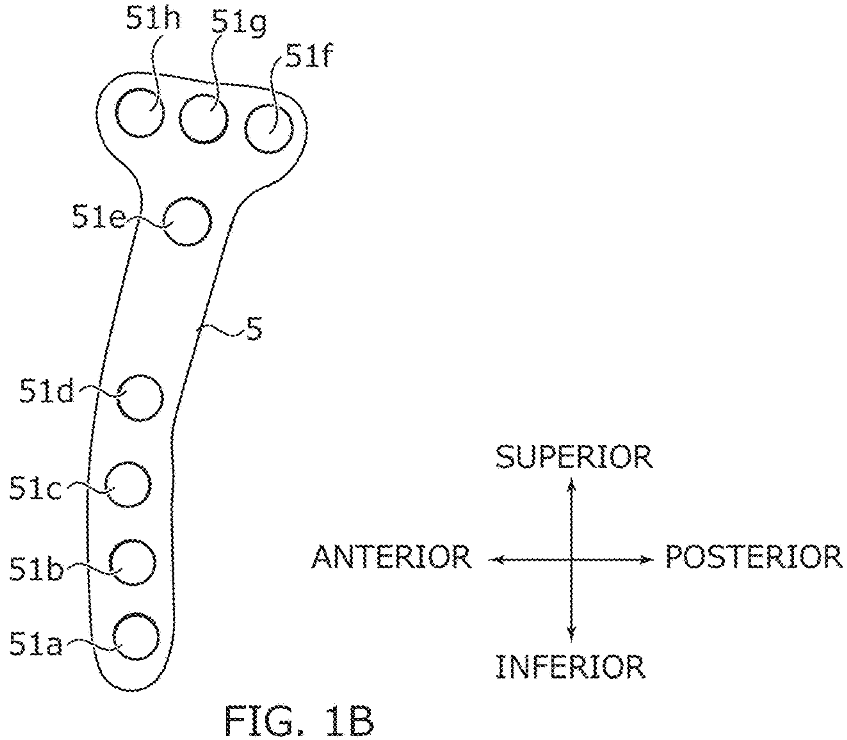

FIGS. 1A and 1B illustrate fixing plate 5 that is fixed to a bone cutting area of tibia T. FIG. 1A illustrates a state in which fixing plate 5 is disposed in a bone cutting area, and FIG. 1B is a plan view of fixing plate 5.

As illustrated in FIGS. 1A and 1B, fixing plate 5 made of metal is disposed in the bone cutting area of tibia T so as to bridge between distal bone piece T1 on the inferior side (the side distal from the knee) of a bone cutting portion and proximal bone piece T2 on the superior side (the side close to the knee) of the bone cutting portion. Fixing plate 5 includes screw bolt holes 51*a* to 51*h* through which screw bolts 52*a* to 52*h* are inserted. Fixing plate 5 is fixed to the bone cutting area of tibia T by distal screw bolts 52*a* to 52*d* fastening a distal portion of fixing plate 5 to distal bone piece T1 and proximal screw bolts 52*e* to 52*h* fastening a proximal portion of fixing plate 5 to proximal bone piece T2.

Generally, in the CWHTO, correction is performed by applying an instrument (for example, the osteotomy assistance jig disclosure in PTL 1) to the lateral side of the tibia, removing a wedge-shaped bone piece whose lateral side is wide and whose medial side is narrow, and closing a proximal-side bone cutting surface and a distal-side bone cutting surface.

In the OWHTO, on the other hand, correction is performed, as illustrated in FIG. 1A, by applying an instrument to the medial side of tibia T, performing bone cutting on one bone cutting surface, rotating distal bone piece T1 or proximal bone piece T2 around hinge axis H, which serves as a rotation axis at the time of correction, by predetermined correction angle θ, which is planned, and opening a gap between a proximal-side bone cutting surface and a distal-side bone cutting surface.

In the present embodiment, by preparing preoperative planning by means of template R (see FIG. 5) including information indicating the position and posture of HTO assistance jig 1 and information indicating an osteotomy alignment associated with HTO assistance jig 1 as well as by using HTO assistance jig 1 during an operation, it is possible to accurately reproduce, during the operation, the osteotomy alignment set in the preoperative planning.

Here, the osteotomy alignment is information required in an osteotomy, and includes: hinge axis H which serves as a rotation axis at the time of correction; bone cutting surface S (see FIG. 2) as a target; distal screw bolt fixing positions P1 and proximal screw bolt fixing positions P2 (see FIG. 8) of fixing plate 5 (see FIG. 1A or the like); and the like.

Figure 2:
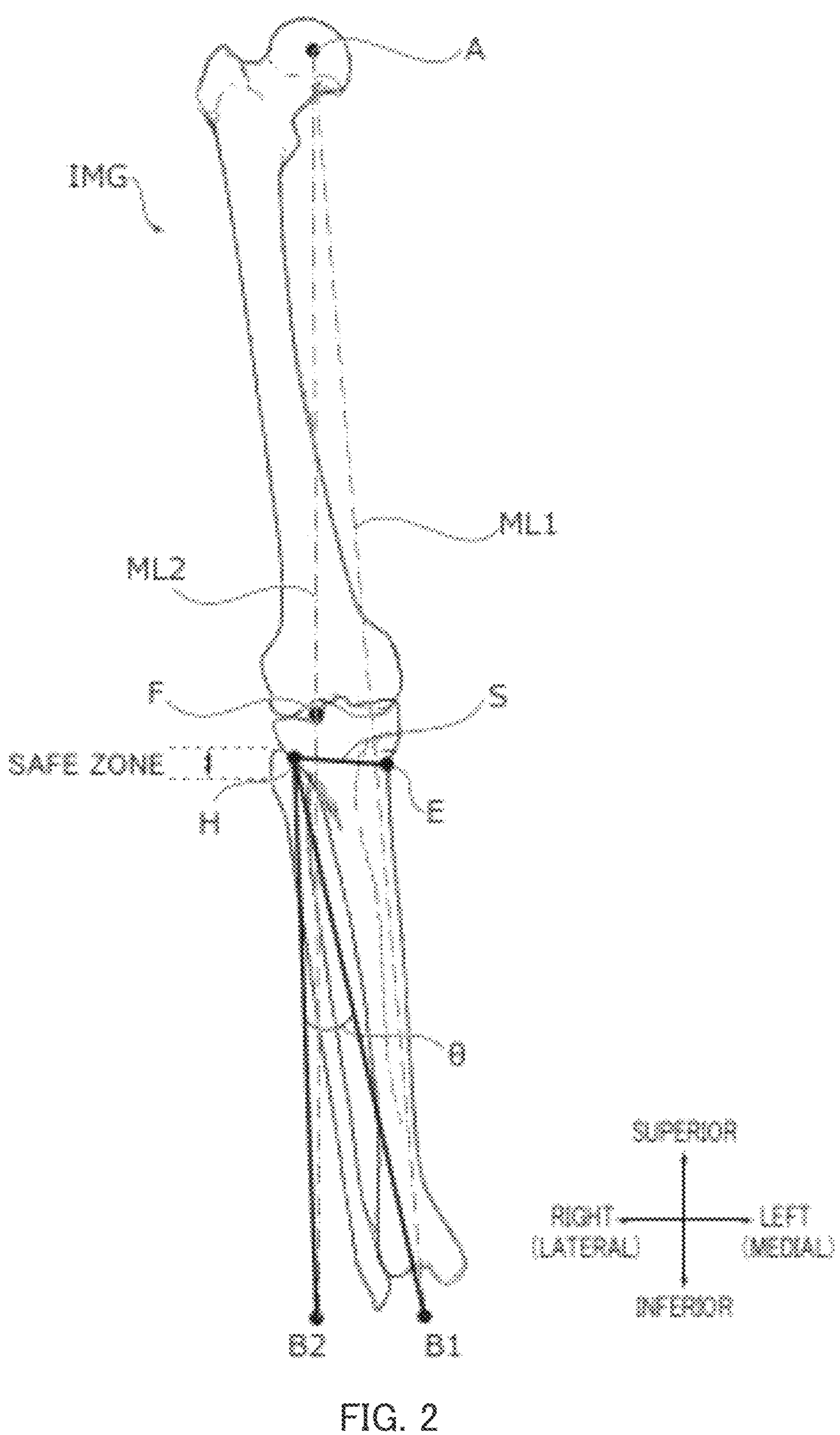
FIG. 2 illustrates an exemplary setting method of hinge axis H, correction angle θ, and bone cutting surface S in preoperative planning.

FIG. 2 illustrates an exemplary setting method of hinge axis H, correction angle θ, and bone cutting surface S in preoperative planning.

In the preoperative planning, as illustrated in FIG. 2, actual functional axis ML1 before correction, which connects femoral head center A and ankle (talus) center B1, and target functional axis ML2, which is ideal, are drawn by utilizing full-length standing lower limb X-ray image IMG as viewed from the anterior side (front side). Target functional axis ML2 is drawn, for example, so as to pass through target function axis passing point F (for example, the lateral edge of the lateral condyle) which is approximately 60 to 65% from the medial edge of the joint surface of the tibia in a case where actual functional axis ML1 is rotated with femoral head center A as a fulcrum and the distance between the medial edge of the joint surface of the tibia and the lateral edge thereof is 100%. In the case of a genu varum, actual functional axis ML1 is medial to target functional axis ML2 as illustrated in FIG. 2.

Then, for example, within a safe zone between the fibular head and the tibiofibular joint, hinge axis His set in a position approximately 5 mm medial to the most proximate portion of the tibiofibular joint. The angle formed by straight line H-B1, which connects hinge axis H and ankle center B1 before correction, and straight line H-B2, which connects hinge axis H and ankle center B2 as a target after correction, serves as correction angle θ. Further, at the medial edge of tibia T, bone-cutting starting point E is set, for example, in a position on the distal side approximately 35 to 40 mm from the joint surface. The line connecting hinge axis H and bone-cutting starting point E serves as a bone cutting line. The bone cutting line serves as a reference line for cutting, and bone cutting surface S is formed by cutting along the bone cutting line. That is, bone cutting surface S is a plane including the bone cutting line.

In a case where HTO assistance jig 1 in the present embodiment is used, bone cutting surface S (bone cutting line) is associated with HTO assistance jig 1. In the preoperative planning, hinge axis His decided by an operation of an operator, and bone cutting surface S is then automatically set by aligning template R (see FIG. 5), in which HTO assistance jig 1 is drawn by using hinge axis H as a reference, with an optimum position.

For example, in a case where preoperative planning is performed by using a digital X-ray image and a digital template, only digitizing outline points (three points) of the femoral head, medial and lateral edge points (two points in total) of the tibia, and medial and lateral edge points (two points in total) of the ankle allows three points of femoral head center A, target function axis passing point F, and ankle center B1 before correction to be obtained based on the digitized feature points by computer calculation, and actual functional axis ML1, target functional axis ML2, and ankle center B2 after correction are automatically calculated.

Then, bone cutting surface S is automatically set when hinge axis H is set manually and template R is disposed in an optimum position. Further, correction angle θ is automatically calculated from hinge axis H and ankle centers B1 and B2 before and after correction.

Figure 3:
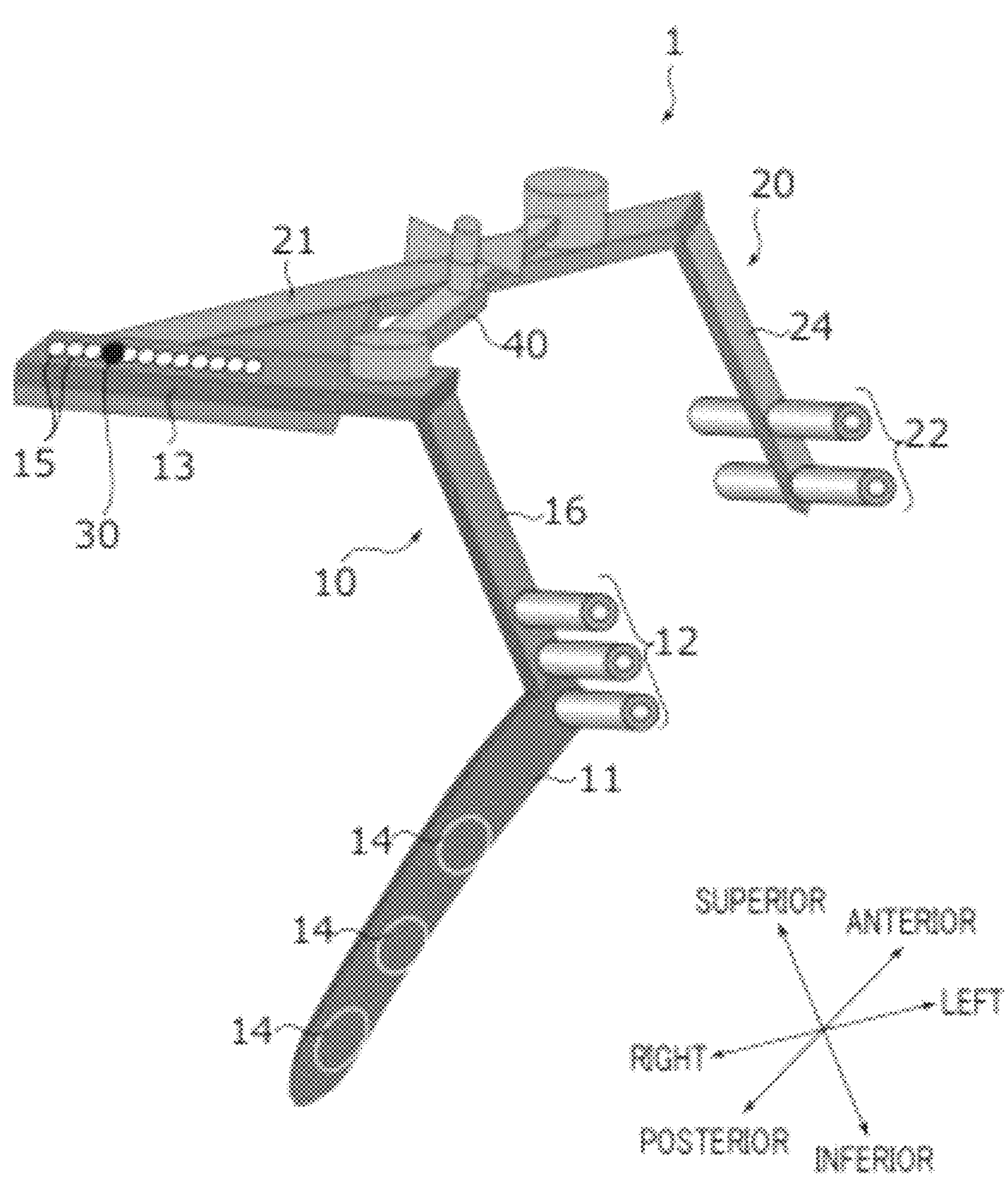
FIG. 3 is a perspective view of an HTO assistance jig according to an embodiment.
Figure 4A:
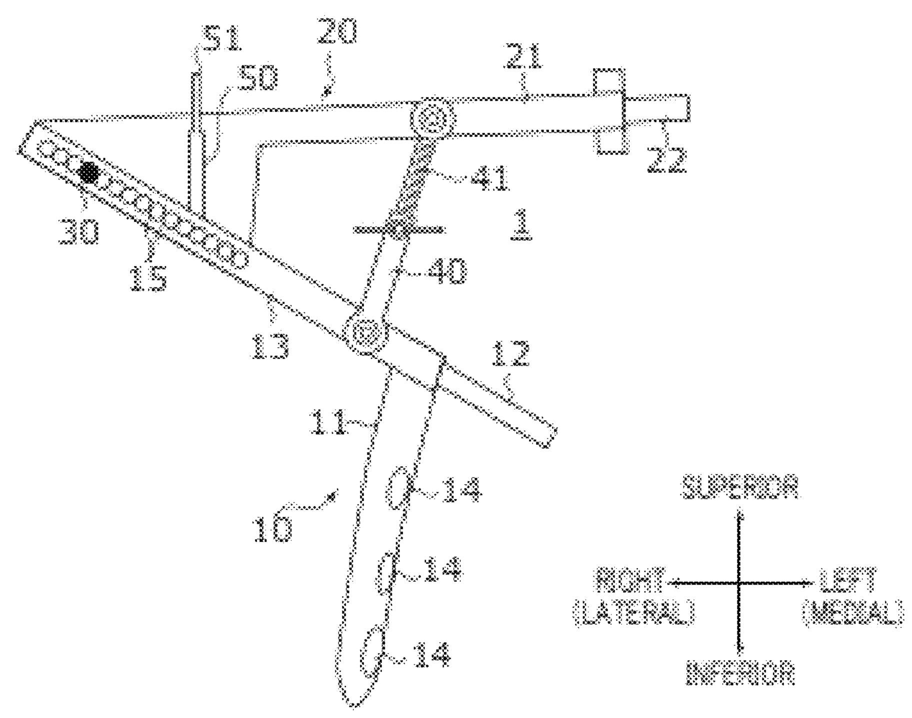
FIGS. 4A and 4B are plan views of the HTO assistance jig.
Figure 4B:
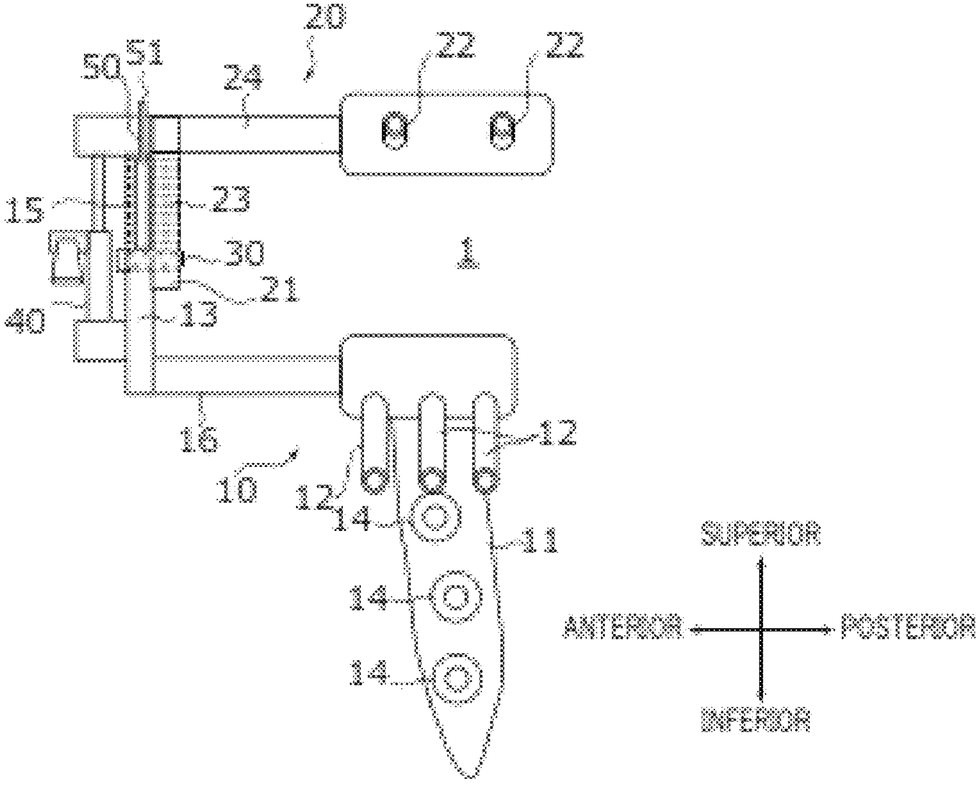

FIG. 3 is a perspective view of HTO assistance jig 1 according to the embodiment. FIG. 4A is a plan view of HTO assistance jig 1 as viewed from the anterior side, and FIG. 4B is a plan view of HTO assistance jig 1 as viewed from the left side. Note that, FIGS. 3, 4A, and 4B schematically illustrate HTO assistance jig 1, and the detailed structure of HTO assistance jig 1 is not limited to the structure illustrated in FIGS. 3, 4A, and 4B.

HTO assistance jig 1 illustrated in FIG. 3 or the like is used in an OWHTO for the tibia of the right leg. The HTO assistance jig used in an OWHTO for the tibia of the left leg has a symmetrical structure with respect to the sagittal plane perpendicular to the left-right direction.

HTO assistance jig 1 is designed such that hinge axis H, bone cutting surface S, distal screw bolt fixing positions P1, and proximal screw bolt fixing positions P2, each of which is set in the preoperative planning, can be set. In a case where there is a plurality of fixing plates 5 having different shapes or with different screw bolt fixing positions, HTO assistance jig 1 is provided for each fixing plate 5.

Specifically, in the osteotomy alignment described above, bone cutting surface S, distal screw bolt fixing positions P1, and proximal screw bolt fixing positions P2 are set in advance in association with HTO assistance jig 1. In addition, HTO assistance jig 1 is configured such that hinge axis H is selected and set from a plurality of hinge candidates. Note that, proximal screw bolt fixing positions P2 are configured to be adjustable as appropriate based on correction angle θ set in the preoperative planning.

As illustrated in FIG. 3 or the like, HTO assistance jig 1 includes first registration member 10, second registration member 20, hinge axis member 30, coupling member 40, reference antenna 50, and the like. Note that, illustration of reference antenna 50 is omitted in FIG. 3. Each member constituting HTO assistance jig 1 is formed of, for example, a metal material such as titanium.

First registration member 10 is a member for positioning HTO assistance jig 1 with respect to tibia T and setting bone cutting surface S and distal screw bolt fixing positions P1. First registration member 10 includes positioning plate 11, bone cutting guide section 12, first hinge setting plate 13, and distal screw bolt guide section 14.

Positioning plate 11 is a portion that serves as a reference for the disposition of HTO assistance jig 1, and abuts on the medial side of the tibia during an operation to position HTO assistance jig. The surface of positioning plate 11, which abuts on the medial side of the tibia, has a shape that allows HTO assistance jig 1 to be held in a stable posture when HTO assistance jig 1 is installed on tibia T.

Bone cutting guide section 12 is a portion for setting bone cutting surface S, and has a tubular shape extending in the bone cutting direction. In the present embodiment, three bone cutting guide sections 12 are disposed at the proximal end of positioning plate 11. Guide pins 61 for bone cutting (so-called K-wires; see FIG. 11) are inserted into distal bone piece T1 of tibia T via bone cutting guide sections 12. Note that, a plurality of bone cutting guide sections 12 may be provided such that bone cutting surface S is determined by guide pins 61 that are inserted via bone cutting guide sections 12.

First hinge setting plate 13 is a plate-like member that includes a main surface (a main surface extending in the superior-inferior direction and in the left-right direction) orthogonal to the anterior-posterior direction. First hinge setting plate 13 is coupled to positioning plate 11 by coupling arm 16 extending in the anterior-posterior direction.

First hinge setting plate 13 includes a plurality of first hinge candidate holes 15 extending in the anterior-posterior direction. The plurality of first hinge candidate holes 15 is arranged on the same straight line as a guide direction indicated by bone cutting guide sections 12. The guide direction indicated by bone cutting guide sections 12 is nothing but the extending direction of the bone cutting line. That is, when HTO assistance jig 1 is viewed from the anterior side, first hinge candidate holes 15 are present on the extension of bone cutting guide sections 12, that is, on the bone cutting line. The inner diameter of first hinge candidate holes 15 is, for example, 1.5 to 2.0 mm. In FIG. 3 or the like, first hinge setting plate 13 extends along the arrangement direction of first hinge candidate holes 15, but the planar shape of first hinge setting plate 13 as viewed from the anterior-posterior direction is not particularly limited.

Distal screw bolt guide section 14 is a portion for setting distal screw bolt fixing positions P1 of fixing plate 5 in distal bone piece T1 divided by bone cutting. In the present embodiment, distal screw bolt guide section 14 is constituted by three holes provided in positioning plate 11. Distal screw bolt guide sections 14 are provided corresponding to distal screw bolt holes 51*a* to 51*c* (see FIG. 1B) of fixing plate 5.

Note that, distal screw bolt guide sections 14 may be provided corresponding to two or all four of four distal screw bolt holes 51*a* to 51*d* of fixing plate 5. That is, a plurality of distal screw bolt guide sections 14 may be provided such that the fixing position of the distal portion of fixing plate 5 is determined by guide pins 62 (see FIG. 11) for distal screw bolts, which are inserted via distal screw bolt guide sections 14.

Second registration member 20 is a member for setting proximal screw bolt fixing positions P2 with respect to proximal bone piece T2. Second registration member 20 includes second hinge setting plate 21 and proximal screw bolt guide section 22.

In the same manner as first hinge setting plate 13, second hinge setting plate 21 is a plate-like member that includes a main surface (a main surface extending in the superior-inferior direction and in the left-right direction) orthogonal to the anterior-posterior direction. Second hinge setting plate 21 is coupled to proximal screw bolt guide section 22 by coupling arm 24 extending in the anterior-posterior direction.

Second hinge setting plate 21 includes a plurality of second hinge candidate holes 23 extending in the anterior-posterior direction. The plurality of second hinge candidate holes 23 is arranged on a straight line so as to correspond to first hinge candidate holes 15 provided in first hinge setting plate 13. The inner diameter of second hinge candidate holes 23 is, for example, 1.5 to 2.0 mm. In the same manner as first hinge setting plate 13, the planar shape of second hinge setting plate 21 as viewed from the anterior-posterior direction is not particularly limited.

Proximal screw bolt guide section 22 is a portion for setting proximal screw bolt fixing positions P2 of fixing plate 5 in proximal bone piece T2 divided by bone cutting. In the present embodiment, proximal screw bolt guide section 22 is constituted by two guide tubes. Proximal screw bolt guide sections 22 are provided corresponding to proximal screw bolt holes 51*f* and 51*h* (see FIG. 1B) of fixing plate 5.

Note that, proximal screw bolt guide sections 22 may be provided corresponding to all three of three distal screw bolt holes 51*a* to 51*c* of fixing plate 5. That is, a plurality of proximal screw bolt guide sections 22 may be provided such that the fixing position of the proximal portion of fixing plate 5 is determined by guide pins 63 (see FIG. 11) for proximal screws, which are inserted via proximal screw bolt guide sections 22.

First registration member 10 and second registration member 20 are disposed such that a portion of first hinge setting plate 13, in which first hinge candidate holes 15 are disposed, and a portion of second hinge setting plate 21, in which second hinge candidate holes 23 are disposed, overlap in the anterior-posterior direction, and are coupled by hinge axis member 30 and coupling member 40.

Hinge axis member 30 couples first registration member 10 to second registration member 20 in the anterior-posterior direction, and supports second registration member 20 in a rotatable manner with respect to first registration member 10 within the coronal plane. Hinge axis member 30 is configured to be insertable into and detachable from first hinge candidate hole 15 of first registration member 10 and second hinge candidate hole 23 of second registration member 20. The pair of first hinge candidate hole 15 and second hinge candidate hole 23, through which hinge axis member 30 is inserted, is selected according to the preoperative planning. That is, a pivot axis constituted by hinge axis member 30 is variable along the bone cutting line which is the arrangement direction of first hinge candidate holes 15.

Coupling member 40 is a member for coupling first registration member 10 to second registration member 20 and fixing relative postures of first registration member 10 and second registration member 20 with respect to each other. Further, coupling member 40 functions as a posture adjustment section that rotates second registration member 20 with respect to first registration member 10 with hinge axis member 30 as a fulcrum to change the relative postures of first registration member 10 and second registration member 20 with respect to each other. Note that, HTO assistance jig 1 may include a posture adjustment section separate from coupling member 40.

Coupling member 40 is configured to be capable of extending and contracting a coupling length of coupling member 40, and is configured such that both end sections thereof rotate with respect to first hinge setting plate 13 and second hinge setting plate 21 along with the extension and contraction. Further, coupling member 40 is configured to be capable of fixing the coupling length.

Further, coupling member 40 is provided with scale 41 indicating the coupling length, and the rotation angle of second hinge setting plate 21 with respect to first hinge setting plate 13 with hinge axis member 30 as a fulcrum is associated with scale 41. That is, it is configured such that the rotation angle of second hinge setting plate 21 with respect to first hinge setting plate 13 with hinge axis member 30 as a fulcrum can be recognized based on the position of hinge axis member 30 and the coupling length.

Note that, HTO assistance jig 1 may include an angle detection section (illustration is omitted), such as an angle sensor, that automatically detects the rotation angle of second registration member 20 with respect to first registration member 10.

Reference antenna 50 is, for example, a rod-shaped member extending substantially in the superior-inferior direction, and is attached to the superior surface of first hinge setting plate 13. Reference antenna 50 is used to define the position of HTO assistance jig 1 with respect to tibia T in the superior-inferior direction. The position of HTO assistance jig 1 in the superior-inferior direction is determined by aligning leading-end section 51 on the proximal side of reference antenna 50 with a reference plane for bone cutting (for example, the proximal lateral joint surface of the tibia).

Reference antenna 50 is, for example, configured to be capable of extending and contracting, and the position of leading-end section 51 can be adjusted. That is, reference antenna 50 is configured such that the position of HTO assistance jig 1 in the superior-inferior direction, which is defined by the length of reference antenna 50, is variable. Thus, a case where a position adjustment of fixing plate 5, that is, a position adjustment of HTO assistance jig 1 in the superior-inferior direction is performed in the preoperative planning can be easily addressed, and it is possible to install HTO assistance jig 1 on tibia T as in the preoperative planning.

In the initial state of HTO assistance jig 1, first hinge candidate holes 15 and second hinge candidate holes 23 coincide in the anterior-posterior direction. The "initial state" is a state in which distal screw bolt guide sections 14 and proximal screw bolt guide sections 22 correspond to the distal screw bolt holes and the proximal screw bolt holes of fixing plate 5, respectively. The rotation angle of second hinge setting plate 21 with respect to first hinge setting plate 13 is expressed by using the initial state as a reference (the rotation angle of 0°).

Hereinafter, the preparation of preoperative planning and the actual operation in a case where the OWHTO is performed by using HTO assistance jig 1 will be described. In the present embodiment, an example of preoperative planning using a 2D image will be described.

Figure 5:
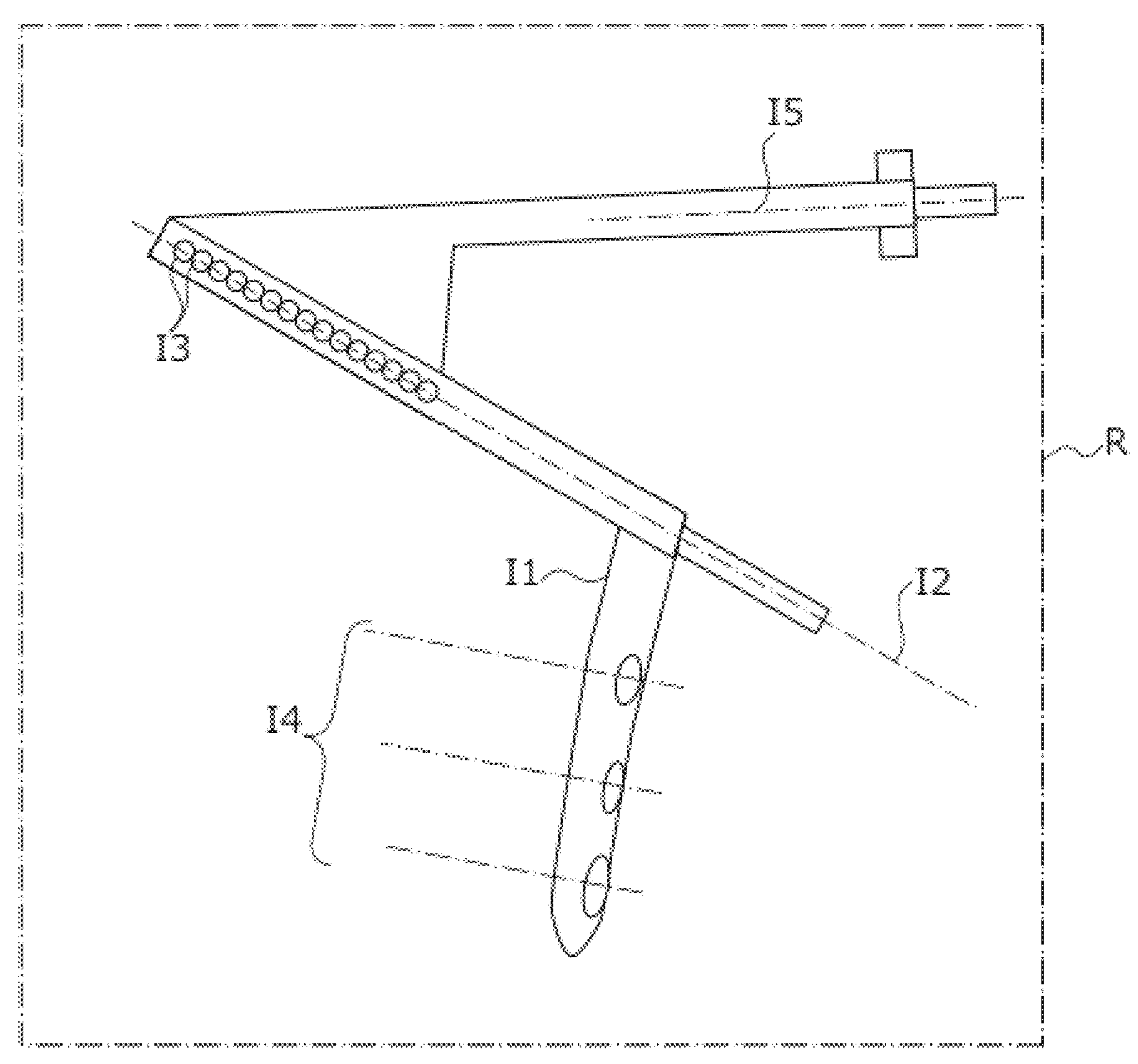
FIG. 5 illustrates an exemplary template used in the preoperative planning.

In the preoperative planning, template R as illustrated in FIG. 5 is used. For example, a film-like template is used in a case where the preoperative planning is performed by performing drawing using an X-ray film in an analogous manner. Further, for example, a digital template is used in a case where the preoperative planning is performed by computer calculation using a digital X-ray image.

In template R, registration information I1 indicating the position and posture of HTO assistance jig 1, bone cutting surface information I2 indicating the bone cutting surface defined by HTO assistance jig 1, and hinge candidate information I3 indicating hinge candidates are drawn. In addition, in template R, distal screw bolt information I4 indicating distal screw bolt fixing positions P1 and proximal screw bolt information I5 indicating proximal screw bolt fixing positions P2 (insertion direction) are drawn. Each information is drawn in an aspect in which each information can be easily visually recognized in terms of grasping the positional relationship with tibia T. In the case of the digital template, each information includes two-dimensional coordinate data.

In FIG. 5, registration information I1 is indicated with an image in which a state in which HTO assistance jig 1 is viewed from the anterior side is modeled. Each of bone cutting surface information I2, distal screw bolt information I4, and proximal screw bolt information I5 is indicated with a dotted line. Further, hinge candidate information I3 is indicated with circle images. Note that, the display aspect of registration information I1 is not limited to that illustrated in FIG. 5. That is, at least information indicating the tibia abutment surface of positioning plate 11 may be included such that the installation position of HTO assistance jig 1 with respect to tibia T can be determined.

Bone cutting surface information I2, hinge candidate information I3, distal screw bolt information I4, and proximal screw bolt information I5 are associated with registration information I1. That is, when the position or posture in registration information I1 changes, the positions or postures in bone cutting surface information I2, hinge candidate information I3, distal screw bolt information I4, and proximal screw bolt information I5 also change correspondingly. Further, proximal screw bolt information I5 is configured to be rotatable around hinge candidate information I3 (hinge axis H that is set in the preoperative planning).

Hereinafter, the preoperative planning in the present embodiment will be described with reference to FIGS. 6 to 9. Note that, FIGS. 6 to 9 illustrate an enlarged bone cutting area.

In the preoperative planning, outline points (three points) of the femoral head, medial and lateral edge points (two points in total) of the tibia, and medial and lateral edge points (two points in total) of the ankle are digitalized on a full-length standing lower limb X-ray image as described with reference to FIG. 2. Three points of femoral head center A, target function axis passing point F, and ankle center B1 before correction are obtained based on the digitized feature points by computer calculation, and actual functional axis ML1, target functional axis ML2, and ankle center B2 after correction are automatically calculated.

Figure 6:
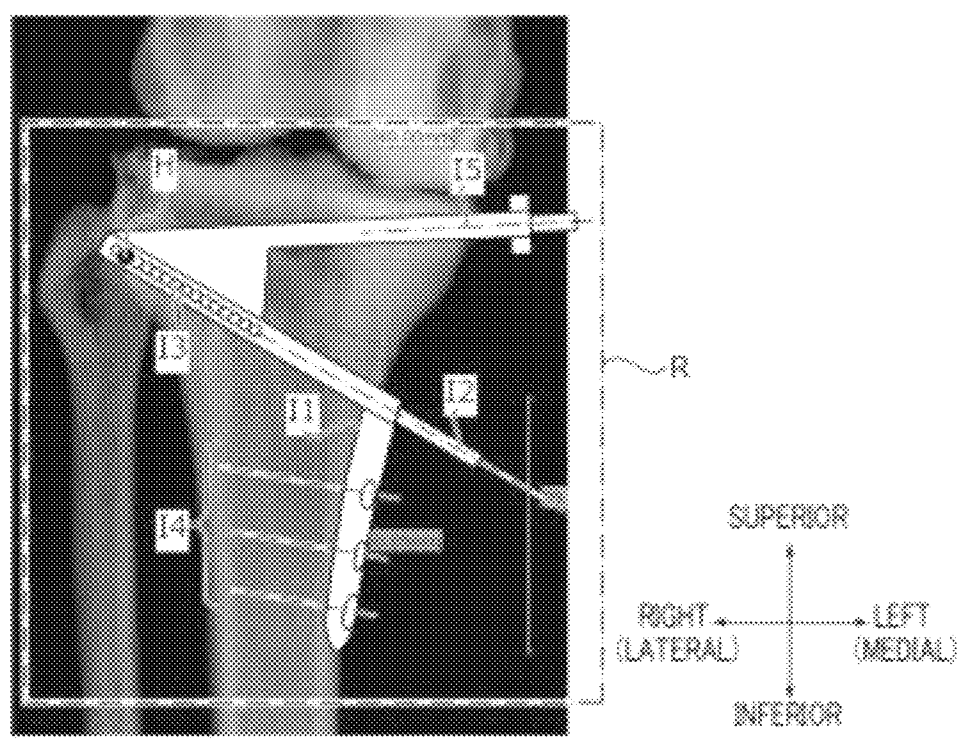
FIG. 6 is a diagram provided for describing the preoperative planning according to the embodiment.

Then, when hinge axis H is set manually, correction angle θ is automatically calculated from hinge axis H and ankle centers B1 and B2 before and after correction. Thereafter, bone cutting surface S is automatically decided when template R is disposed in an optimum position as illustrated in FIG. 6.

Specifically, template R of HTO assistance jig 1 is superposed on an X-ray image, and the position and posture of template R are adjusted while referring to registration information I1 and hinge candidate information I3 such that positioning plate 11 is compatible with the medial bone cortex of the tibia and hinge axis H that has been set coincides with one of a plurality of hinge candidate holes. In FIG. 6, the second hinge candidate hole from the right side coincides with hinge axis H that has been set.

Figure 7:
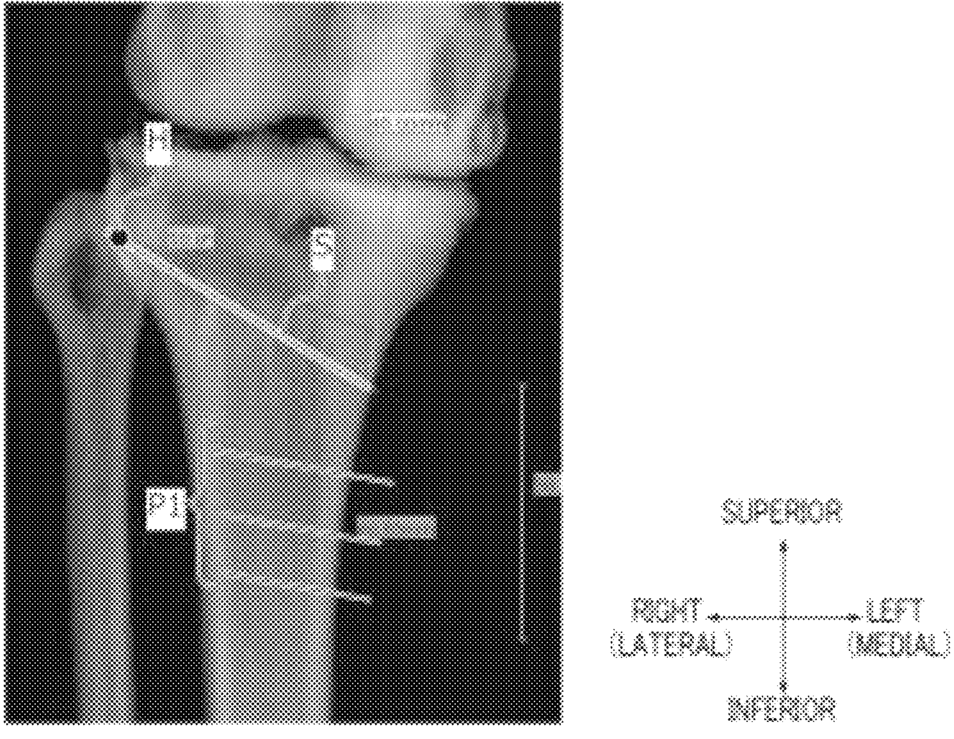
FIG. 7 is a diagram provided for describing the preoperative planning according to the embodiment.
Figure 8:
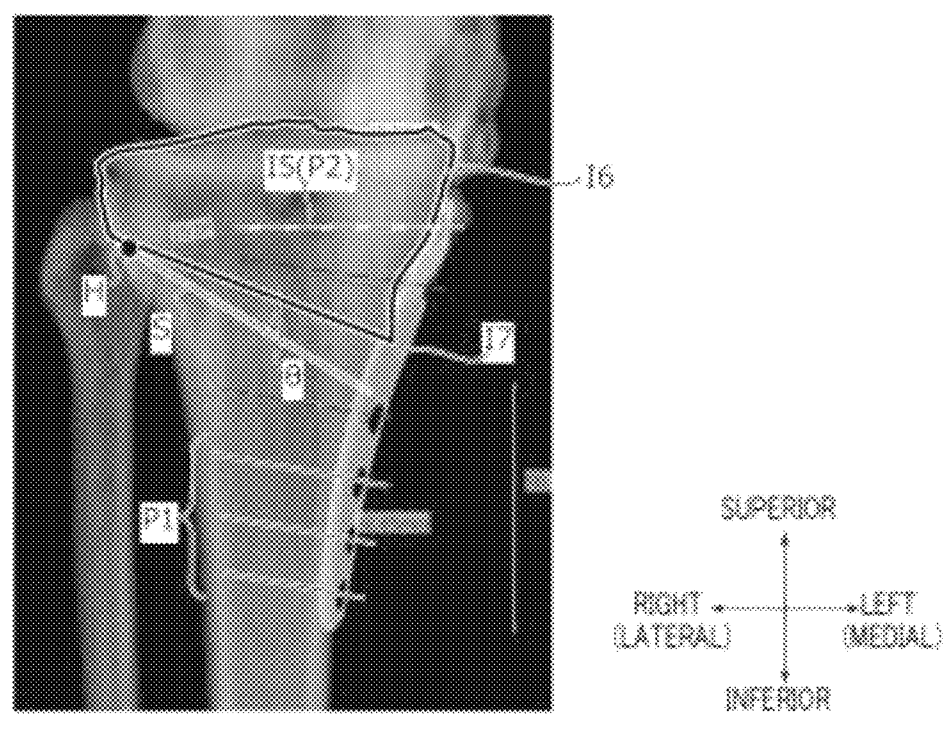
FIG. 8 is a diagram provided for describing the preoperative planning according to the embodiment.

At this point, bone cutting surface S and distal screw bolt fixing positions P1 are tentatively decided as illustrated in FIG. 7. Then, it is configured as illustrated in FIG. 8, and the lower limb alignment after correction and the shape compatibility of fixing plate 5 are confirmed.

Specifically, proximal bone piece image I6 when bone cutting is performed on bone cutting surface S that has been tentatively decided is displayed in a state in which proximal bone piece image I6 is rotated around hinge axis H by correction angle θ. In addition, model image I7 of fixing plate 5 is superimposed and displayed based on registration information I1.

In a case where the shape compatibility of fixing plate 5 is extremely poor, it is necessary to change fixing plate 5 to another type of fixing plate that differs in size or shape. Accordingly, preoperative planning in a case where HTO assistance jig 1 for the above fixing plate is used is performed anew. By preparing preoperative planning including the shape compatibility between the shape of fixing plate 5 and a plate installation portion after correction, it is possible to prevent correction angle θ from being impaired after fixing plate 5 is installed when the shape incompatibility of fixing plate 5 becomes clear during an operation.

Note that, in the case of a small deviation in the shape compatibility, hinge axis H may be reset. Further, the determination of the compatibility between the bone shape after correction and fixing plate 5 is preferably confirmed not only with the front image illustrated in FIG. 8 as viewed from the anterior-posterior direction, but also with a side surface image as viewed from the left-right direction.

Figure 9:
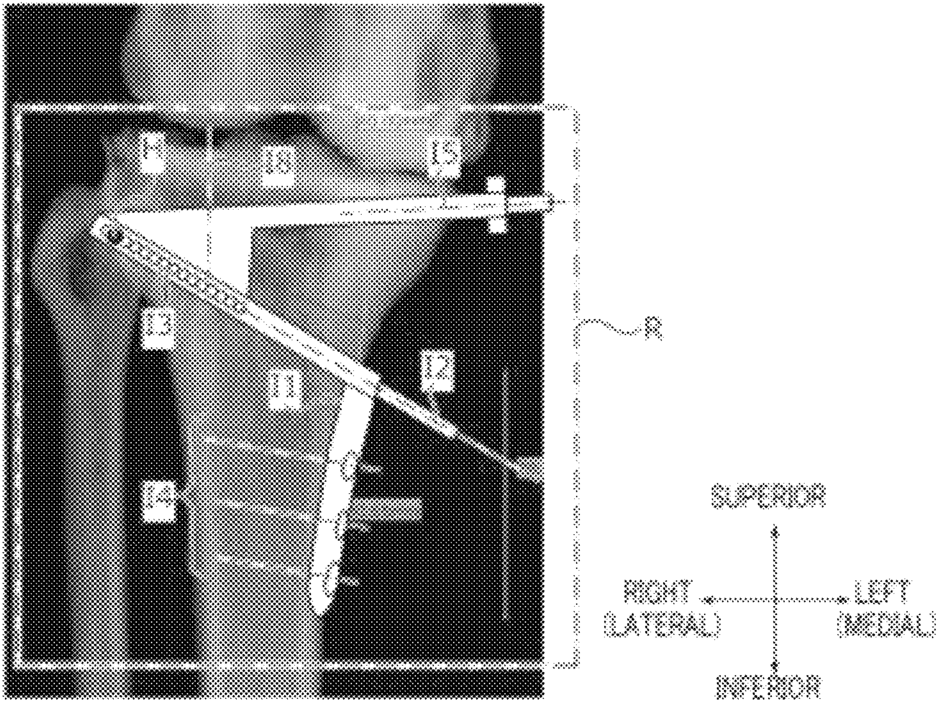
FIG. 9 is a diagram provided for describing the preoperative planning according to the embodiment.

Then, as illustrated in FIG. 9, reference antenna information I8 is added to template R, and the distal and proximal positions (positions in the superior-inferior direction) of HTO assistance jig 1 during an operation are quantitatively decided. Reference antenna information I8 indicates the extending direction of reference antenna 50. For example, by digitalizing the intersection of the proximal lateral joint surface of the tibia and reference antenna information I8, this point is set as the position of leading-end section 50*a* of reference antenna 50, and the length of reference antenna 50 is automatically calculated. In this way, the preoperative planning when the OWHTO is performed using HTO assistance jig 1 is prepared.

FIGS. 10 to 14 are diagrams provided for describing an OWHTO according to the preoperative planning described above. The OWHTO is performed while performing confirmation under X-ray fluoroscopy according to the preoperative planning.

Figure 10:
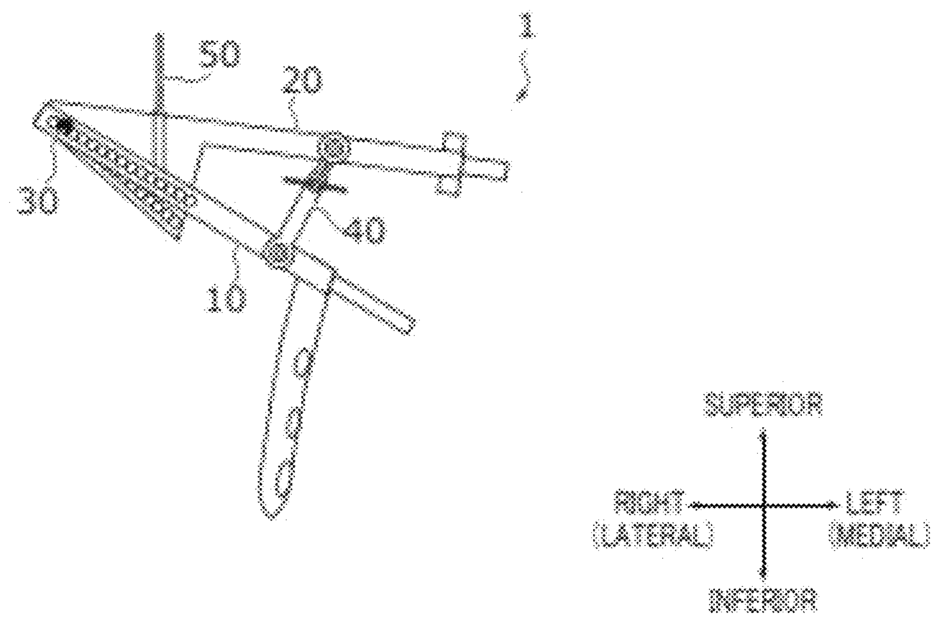
FIG. 10 is a diagram provided for describing a high tibial osteotomy according to the preoperative planning.

As illustrated in FIG. 10, as preliminary processing of the OWHTO, the state of HTO assistance jig 1 is set as in the preoperative planning. Specifically, the length of reference antenna 50 is adjusted as in the preoperative planning. Hinge axis member 30 is inserted through hinge candidate holes selected in the preoperative planning and is fixed in an undroppable manner. In addition, the coupling length of coupling member 40 is adjusted, and second registration member 20 (second hinge setting plate 21) is rotated with respect to first registration member 10 (first hinge setting plate 13) by correction angle θ set in the preoperative planning. Note that, second registration member 20 may be rotated with respect to first registration member 10 by installing HTO assistance jig 1 in the initial state in an optimum position of the bone cutting area, and then adjusting the coupling length of coupling member 40.

Figure 11:
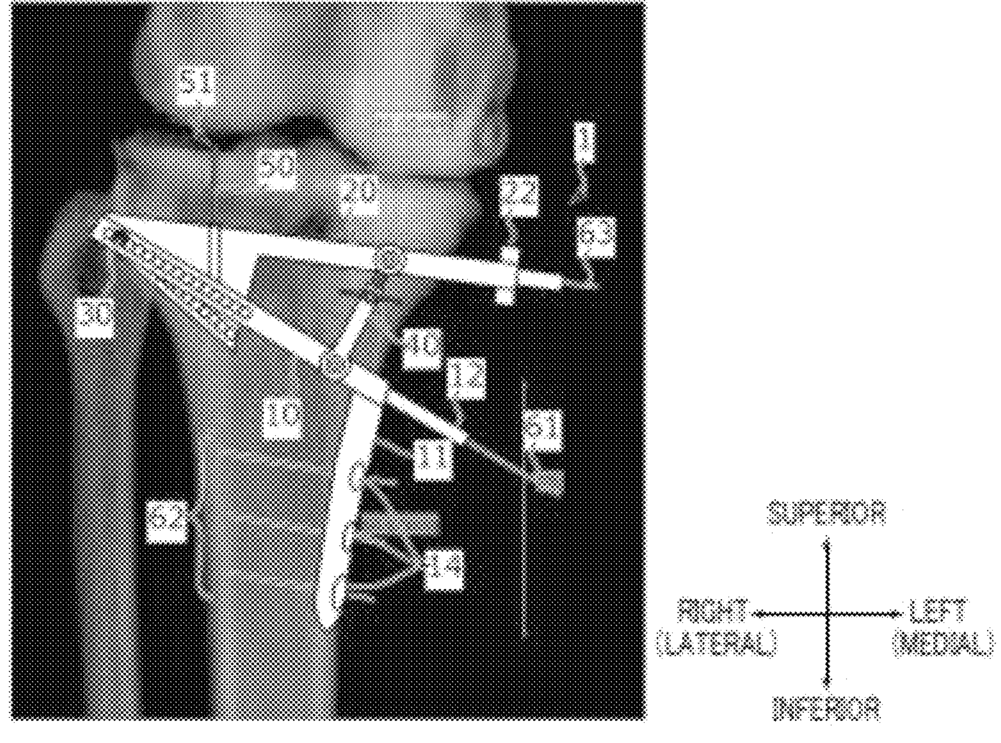
FIG. 11 is a diagram provided for describing the high tibial osteotomy according to the preoperative planning.

Then, as illustrated in FIG. 11, HTO assistance jig 1 is installed on a predetermined portion of tibia T. Specifically, leading-end section 50*a* of reference antenna 50 is aligned with the same level as the proximal lateral joint surface of the tibia while aligning the tibia abutment surface of positioning plate 11 with the diaphyseal portion of the tibia. Thus, the position of HTO assistance jig 1 with respect to tibia T is determined. In addition, the installation position of HTO assistance jig 1 is reproduced as in the preoperative planning, and HTO assistance jig 1 is held in a stable posture.

Next, an osteotomy alignment is set using HTO assistance jig 1 installed in an optimum position of the bone cutting area. Since hinge axis H, bone cutting surface S, distal screw bolt fixing positions P1, and proximal screw bolt fixing positions P2, each of which has been set in the preoperative planning, are associated with HTO assistance jig 1, the osteotomy alignment as in the preoperative planning can be easily set.

Figure 12:
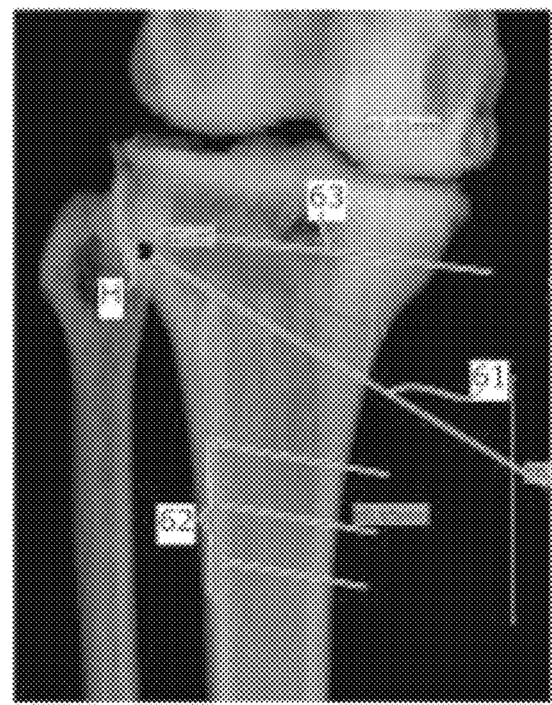
FIG. 12 is a diagram provided for describing the high tibial osteotomy according to the preoperative planning.
Figure 12:
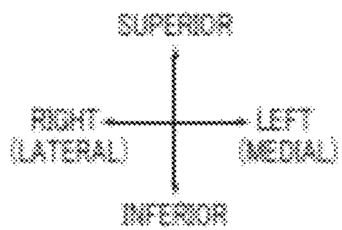

Specifically, as illustrated in FIG. 12, guide pins 61 to 63 are inserted into tibia T.

Three guide pins 61 for bone cutting are inserted via bone cutting guide sections 12 of HTO assistance jig 1, and are utilized as an indicator when bone cutting surface S is formed. Guide pins 62 for distal screw bolts are inserted into distal bone piece T1 via distal screw bolt guide sections 14, and are utilized as an indicator when distal screw bolts 52*a* to 52*d* are fixed. Two guide pins 63 for proximal screw bolts are inserted via proximal screw bolt guide sections 22, and are utilized as an indicator when proximal screw bolts 52*f* and 52*h* are fixed.

As described above, by using HTO assistance jig 1, bone cutting surface S, and distal screw bolt fixing positions P1 and proximal screw bolt fixing positions P2 of fixing plate 5 can be set in a stable state before bone cutting. Further, since the direction in which proximal screw bolt holes 51*f* to 51*h* of fixing plate 5 face after correction (after distal bone piece T1 is rotated by correction angle θ) is indicated by proximal screw bolt guide sections 22 with an extremely simple operation of rotating second registration member 20 with respect to first registration member 10, it is possible to easily set not only distal screw bolt fixing positions P1, but also proximal screw bolt fixing positions P2. Then, since fixing plate 5 is fixed by using screw bolt fixing positions P1 and P2 set before bone cutting, a possible mismatch that may occur at the bone cutting surface can be corrected as in the preoperative planning.

Figure 13:
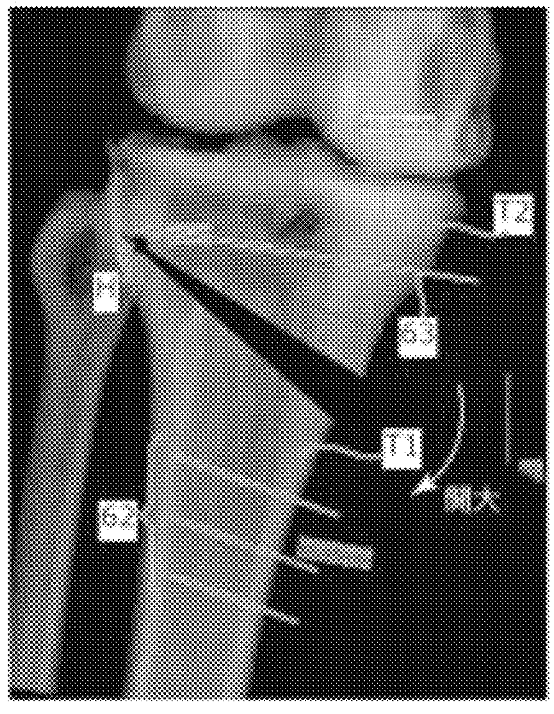
FIG. 13 is a diagram provided for describing the high tibial osteotomy according to the preoperative planning.
Figure 13:
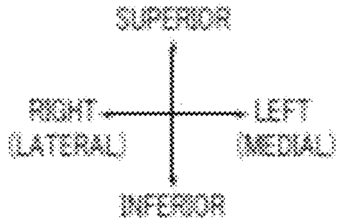

Next, as illustrated in FIG. 12, HTO assistance jig 1 is detached, and bone cutting is performed from the medial side of the tibia on the left side toward hinge axis H by using guide pins 61 for bone cutting as an indicator. Then, as illustrated in FIG. 13, distal bone piece T1 is rotated to the distal side with hinge axis Has a fulcrum to open. Thus, tibia T is bent to the lateral side by correction angle θ and correction is performed.

Figure 14:
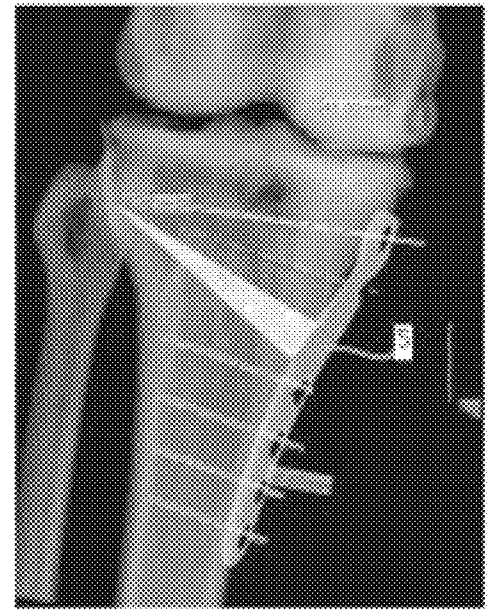
FIG. 14 is a diagram provided for describing the high tibial osteotomy according to the preoperative planning.
Figure 14:
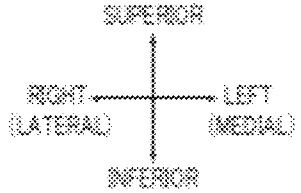

Next, as illustrated in FIG. 14, fixing plate 5 is installed so as to extend over distal bone piece T1 and proximal bone piece T2, and is fixed by distal screw bolts 52*a* to 52*d* and proximal screw bolts 52*e* to 52*h*. Distal screw bolts 52*a* to 52*d* and proximal screw bolts 52*e* to 52*h* are constituted by, for example, hollow bolts, and can be fixed while being inserted through guide pins 62 and 63. Note that, artificial bone or autologous bone is filled between the bone cutting surface of distal bone piece T1 and the bone cutting surface of proximal bone piece T2.

In the present embodiment, since distal screw bolt fixing positions P1 and proximal screw bolt fixing positions P2 are set before bone cutting, it is possible to surely fix fixing plate 5 in a proper position, and it is possible to acquire correction as in the preoperative planning. To describe in an extreme manner, even when bone cutting is not performed accurately according to the preoperative planning, it is possible to acquire correction as in the preoperative planning by fixing plate 5 being fixed in an appropriate position. Since appropriate correction is performed regardless of the bone cutting technique of the operator, the stability of corrective osteotomy improves.

The OWHTO is performed in the above-described manner. In the present embodiment, since HTO assistance jig 1 is associated with an osteotomy alignment set in preoperative planning, the osteotomy alignment as in the preoperative planning is reproduced during an operation by adjusting and installing HTO assistance jig 1 as in the preoperative planning.

As described above, HTO assistance jig 1 (osteotomy assistance jig) according to the present embodiment is an osteotomy assistance jig used in a long bone corrective osteotomy, and includes: first registration member 10; second registration member 20, hinge axis member 30 that supports second registration member 20 in a rotatable manner with respect to first registration member 10; and coupling member 40 that couples first registration member 10 to second registration member 20, and fixes relative postures of first registration member 10 and second registration member 20 with respect to each other. First registration member 10 includes: positioning plate 11 that abuts on tibia T (long bone); bone cutting guide sections 12 for a setting bone cutting surface; first hinge setting plate 13 that includes a plurality of first hinge candidate holes 15 arranged on the same straight line as the guide direction of bone cutting guide sections 12 in a plan view viewed from the anterior-posterior direction; and distal screw bolt guide sections 14 for setting distal screw bolt fixing positions P1 of fixing plate 5 in distal bone piece T1 between proximal bone piece T2 and distal bone piece T1 that are divided by bone cutting. Second registration member 20 includes: second hinge setting plate 21 that includes a plurality of second candidate holes 23 corresponding to the plurality of first hinge candidate holes 15; and proximal screw bolt guide sections 22 for setting proximal screw bolt fixing positions P2 of fixing plate 5 in proximal bone piece T2. First hinge candidate holes 15 coincide with second candidate holes 23 in the anterior-posterior direction in the initial state, and hinge axis member 30 is inserted through one of a plurality of pairs of the plurality of first hinge candidate holes 15 and the plurality of second hinge candidate holes 23.

According to HTO assistance jig 1, since an osteotomy alignment is defined by HTO assistance jig 1, it is possible to perform preoperative planning by using a template in which HTO assistance jig 1 is modeled, and it is possible to accurately reproduce, during an operation, the osteotomy alignment set in the preoperative planning by performing an HTO by using HTO assistance jig 1. Further, since hinge axis H set according to the case can be set by selecting from a plurality of hinge candidate holes in the preoperative planning, it is possible to cope with the OWHTO in which the setting of hinge axis His important.

In addition, proximal screw bolt fixing positions P2 with respect to proximal bone piece T2 and distal screw bolt fixing positions P1 with respect to distal bone piece T1 can be confirmed in advance in the preoperative planning, and an appropriate osteotomy alignment including the fixing position of fixing plate 5 can be set. Further, it is possible to surely fix fixing plate 5 to a proper position after bone cutting to acquire correction as in the preoperative planning.

In addition, in HTO assistance jig 1, coupling member 40 functions as a posture adjustment section that rotates second registration member 20 with respect to first registration member 10 with hinge axis member 30 as a fulcrum to change the relative postures. Specifically, coupling member 40 is configured to be capable of extending and contracting a coupling length of coupling member 40, and the coupling length is associated with the rotation angle of second registration member 20 with respect to first registration member 10. Thus, proximal screw bolt guide sections 22 can be easily fixed in positions corresponding to correction angle θ.

In addition, HTO assistance jig 1 further includes reference antenna 50 disposed in first registration member 10 and for defining the position of HTO assistance jig 1 in the superior-inferior direction. Further, the position of HTO assistance jig 1 in the superior-inferior direction, which is defined by reference antenna 50, is variable. Thus, it is easily possible to address a case where a position adjustment of fixing plate 5, that is, a position adjustment of HTO assistance jig 1 in the superior-inferior direction is performed in preoperative planning, and it is possible to install HTO assistance jig 1 with respect to tibia T as in the preoperative planning.

Further, HTO assistance jig 1 according to the embodiment has the following features alone or in appropriate combination.

That is, HTO assistance jig 1 (osteotomy assistance jig) is an osteotomy assistance jig used to set fixing positions P1 and P2 of distal screw bolts 52*a* to 52*d* and proximal screw bolts 52*e* to 52*h* for fixing fixing plate 5 to tibia T (long bone) after bone cutting, and includes: first registration member 10 that includes positioning plate 11 serving as a disposition reference, and sets fixing positions P1 of distal screw bolts 52*e* to 52*h*; and second registration member 20 that is connected to first registration member 10 so as to be pivotable with respect to first registration member 10 at an arbitrarily pivot angle around a pivot axis (hinge axis member 30) set on a bone cutting line serving as a reference for cutting, and sets fixing positions P2 of proximal screw bolts 52*e* to 52*h*. Fixing positions P1 and P2 of distal screw bolts 52*a* to 52*d* and proximal screw bolts 52*e* to 52*h* are set based on the position of first registration member 10 and a connection position and a connection angle of second registration member 20 with respect to first registration member 10.

In HTO assistance jig 1 (osteotomy assistance jig), hinge axis member 30 (pivot axis) is variable along the bone cutting line.

HTO assistance jig 1 (osteotomy assistance jig) includes hinge axis member 30 that pivotably supports second registration member 20 with respect to first registration member 10. First registration member 10 includes: first hinge setting plate 13 that includes a plurality of first hinge candidate holes 15 arranged on the bone cutting line in a plan view viewed from the anterior-posterior direction; and distal screw bolt guide sections 14 for setting fixing positions P1 of distal screw bolts 52*a* to 52*d*. Second registration member 20 includes: second hinge setting plate 21 that includes a plurality of second hinge candidate holes 23 corresponding to the plurality of first hinge candidate holes 15; and proximal screw bolt guide sections 22 for setting fixing positions P2 of proximal screw bolts 52*e* to 52*h*. Hinge axis member 30 is inserted through one of a plurality of pairs of the plurality of first hinge candidate holes 15 and the plurality of second hinge candidate holes 23.

In HTO assistance jig 1 (osteotomy assistance jig), first registration member 10 includes bone cutting guide sections 12 that define a bone cutting surface that is a plane including the bone cutting line, and fixing positions P1 and P2 of distal screw bolts 52*a* to 52*d* and proximal screw bolts 52*e* to 52*h*, and a position of the bone cutting surface are set based on the position of first registration member 10, and the connection position and the connection angle of second registration member 20 with respect to first registration member 10.

In HTO assistance jig 1 (osteotomy assistance jig), positioning plate 11 abuts on the diaphyseal portion of tibia T.

HTO assistance jig 1 (osteotomy assistance jig) further includes coupling member 40 that couples first registration member 10 to second registration member 20, and fixes relative postures of first registration member 10 and second registration member 20 with respect to each other.

In HTO assistance jig 1 (osteotomy assistance jig), coupling member 40 functions as a posture adjustment section that rotates second registration member 20 with respect to first registration member 10 with hinge axis member 30 (pivot axis) as a fulcrum to change the relative postures.

In HTO assistance jig 1 (osteotomy assistance jig), coupling member 40 is configured to be capable of extending and contracting a coupling length of coupling member 40, and the coupling length is associated with the rotation angle of second registration member 20 with respect to first registration member 10.

HTO assistance jig 1 (osteotomy assistance jig) further includes reference antenna 50 disposed in first registration member 10 and for defining the position of HTO assistance jig 1 in the superior-inferior direction.

In HTO assistance jig 1 (osteotomy assistance jig), the position of HTO assistance jig 1 in the superior-inferior direction, which is defined by reference antenna 50, is variable.

HTO assistance jig 1 (osteotomy assistance jig) further includes an angle detection section that detects a rotation angle when second registration member 20 rotates with respect to first registration member 10 with hinge axis member 30 (pivot axis) as a fulcrum.

Digital template R according to the present embodiment is a digital template in which HTO assistance jig 1 (osteotomy assistance jig) is modeled in a side view. Digital template R to be drawn includes: registration information I1 indicating a position and a posture of HTO assistance jig 1; bone cutting surface information I2 indicating a bone cutting surface associated with HTO assistance jig 1; hinge axis information I3 (candidate position information on the pivot axis); distal screw bolt information I4 (fixing position information on distal screw bolts 52*a* to 52*d*); and proximal screw bolt information I5 (fixing position information on proximal screw bolts 52*e* to 52*h*).

Digital template R includes model image I7 of fixing plate 5 (fixing plate information), in which fixing plate 5 is modeled in a side view.

A long bone corrective osteotomy which is performed by using HTO assistance jig 1 (osteotomy assistance jig) includes: performing preoperative planning by using digital template R; adjusting the connection position and the connection angle of second registration member 20 with respect to first registration member 10 according to the preoperative planning; installing HTO assistance jig 1 (osteotomy assistance jig) in a predetermined portion of tibia T (long bone) according to the preoperative planning; inserting guide pins 62 and 63 into fixing positions P1 and P2 of distal screw bolts 52*a* to 52*d* and proximal screw bolts 52*e* to 52*h* by using HTO assistance jig 1, before cutting tibia T; performing bone cutting of tibia T; positioning fixing plate 5 by using guide pins 62 and 63 as a guide while rotating tibia T after the bone cutting; and inserting distal screw bolts 52*a* to 52*d* and proximal screw bolts 52*e* to 52*h* along guide pins 62 and 63 to fix fixing plate 5 to tibia T.

Although the invention made by the present inventor has been specifically described above based on an embodiment, the present invention is not limited to the above-described embodiment, and modifications can be made without departing from the spirit of the present invention.

For example, HTO assistance jig 1 described in the embodiment includes bone cutting guide sections 12 for setting bone cutting surface S, but may not include bone cutting guide sections 12, and may set bone cutting surface S by using a jig different from HTO assistance jig 1.

Further, in the embodiment, hinge axis H is set by inserting hinge axis member 30 through one pair of hinge candidate holes 15 and 23 selected from the plurality of hinge candidate holes 15 provided in first hinge setting plate 13 and the plurality of hinge candidate holes 23 provided in second hinge setting plate 21, and hinge axis His variable along the bone cutting line which is the arrangement direction of hinge candidate holes 15 and 23, but the setting aspect of hinge axis H is not limited thereto. For example, first hinge setting plate 13 and second hinge setting plate 21 may be provided with an opening having an oblong shape along the bone cutting line to fix hinge axis member 30 to an arbitrary position within the opening.

Further, for example, in HTO assistance jig 1, bone cutting guide sections 12 and first hinge setting plate 13 may be connected to positioning plate 11 such that the guide direction of bone cutting guide sections 12 is changeable in a plurality of stages (for example, three stages). For example, it is configured such that a rotation axis is provided at the proximal end of positioning plate 11, and bone cutting guide sections 12 and the first hinge setting plate 13 can rotate discretely around the rotation axis at a predetermined angle (for example, 5°). In this case, second hinge setting plate 21 is provided with second hinge candidate holes 23 corresponding to all positions that first hinge candidate holes 15 are allowed to take. That is, in HTO assistance jig 1 (osteotomy assistance jig), first hinge setting plate 13 may be configured to be connected to positioning plate 11 such that the bone cutting line is changeable in a plurality of stages, and second hinge setting plate 21 may be configured to include second hinge candidate holes 23 corresponding to all positions that the first hinge candidate holes 15 are allowed to take.

Further, HTO assistance jig 1 (osteotomy assistance jig) may be configured such that at least relative positions and/or relative postures of distal screw bolt guide sections 14 and first hinge candidate holes 15 (pivot axis) are variable. Specifically, HTO assistance jig 1 (osteotomy assistance jig) may be configured such that at least relative positions and/or relative postures between positioning plate 11 and first hinge setting plate 13 (rotation axis setting plate) are variable.

More specifically, in HTO assistance jig 1 (osteotomy assistance jig), the relative positions between positioning plate 11 and first hinge setting plate 13 can be easily changed by configuring such that the length of coupling arm 16 is variable. Further, it may also be configured such that the relative postures between positioning plate 11 and first hinge setting plate 13 can be changed by configuring such that the posture (connection aspect) of coupling arm 16 with respect to positioning plate 11 or first hinge setting plate 13 is variable.

Further, in HTO assistance jig 1 (osteotomy assistance jig), coupling arm 16 may be configured to be interchangeable with respect to positioning plate 11 and first hinge setting plate 13 (rotation axis setting plate) and may be selected from a plurality of variations having different lengths.

Further, in HTO assistance jig 1 (osteotomy assistance jig), first registration member 10 may be configured to be selected from a plurality of variations in which at least relative positions of positioning plate 11 and first hinge setting plate 13 (rotation axis setting plate) and/or relative postures of positioning plate 11 and first hinge setting plate 13 differ.

According to the variations described above, the combinations of the position of hinge axis H, correction angle θ, and the position and size of fixing plate 5 vary depending on the case, but can address a variety of cases widely.

The present invention is applicable not only to the OWHTO described in the embodiment, but also to the CWHOT and a corrective osteotomy of a long bone such as the femur.

It should be understood that the embodiment disclosed herein is illustrative and non-restrictive in every respect. The scope of the present invention is defined by the scope of the claims, rather than the description above, and is intended to include any modifications within the meaning and scope equivalent to the scope of the claims.

The disclosure of Japanese Patent Application No. 2022-007120, filed on Jan. 20, 2022, including the specification, drawings and abstract, is incorporated herein by reference in its entirety.

REFERENCE SIGNS LIST

1 HTO assistance jig (osteotomy assistance jig)
10 First registration member
11 Positioning plate
12 Bone cutting guide section
13 First hinge setting plate
14 Distal screw bolt guide section
20 Second registration member
21 Second hinge setting plate
22 Proximal screw bolt guide section
30 Hinge axis member
40 Coupling member
50 Reference antenna

The invention claimed is:

1. An osteotomy assistance jig used to set a fixing position of a distal screw bolt and a fixing position of a proximal screw bolt, the distal screw bolt and the proximal screw bolt being for fixing a fixing plate to a long bone after bone cutting, the osteotomy assistance jig comprising:

a first registration member that includes a positioning plate serving as a disposition reference, and sets the fixing position of the distal screw bolt; and a second registration member that is connected to the first registration member so as to be pivotable with respect to the first registration member at a pivot axis set on a bone cutting line, and sets the fixing position of the proximal screw bolt, the bone cutting line serving as a reference for cutting, wherein the fixing position of the distal screw bolt and the fixing position the proximal screw bolt are set based on a position of the first registration member, and a connection position and a connection angle of the second registration member with respect to the first registration member wherein the pivot axis is variable along the bone cutting line; a hinge axis member that pivotably supports the second registration member with respect to the first registration member, wherein: the first registration member includes: a first hinge setting plate that includes a plurality of first hinge candidate holes arranged on the bone cutting line in a plan view viewed from an anterior-posterior direction; and a distal screw bolt guide section for setting the fixing position of the distal screw bolt, the second registration member includes: a second hinge setting plate that includes a plurality of second hinge candidate holes corresponding to the plurality of first hinge candidate holes; and a proximal screw bolt guide section for setting the fixing position of the proximal screw bolt, and the hinge axis member is inserted through one of a plurality of pairs of the plurality of first hinge candidate holes and the plurality of second hinge candidate holes and the first hinge setting plate is connected to the positioning plate such that the bone cutting line is changeable in a plurality of stages, and the second hinge setting plate includes the plurality of second hinge candidate holes corresponding to all positions that the plurality of first hinge candidate holes is allowed to take.

2. The osteotomy assistance jig according to claim 1, wherein:

the first registration member includes a bone cutting guide section that defines a bone cutting surface, the bone cutting surface being a plane that includes the bone cutting line, and the fixing position of the distal screw bolt, the fixing position of the proximal screw bolt, and a position of the bone cutting surface are set based on the position of the first registration member, and the connection position and the connection angle of the second registration member with respect to the first registration member.

3. The osteotomy assistance jig according to claim 1, wherein:

the long bone is a tibia, and the positioning plate abuts on a diaphyseal portion of the tibia.

4. The osteotomy assistance jig according to claim 1, further comprising a coupling member that couples the first registration member to the second registration member, and fixes relative postures of the first registration member and the second registration member with respect to each other.

5. The osteotomy assistance jig according to claim 4, wherein the coupling member functions as a posture adjustment section that rotates the second registration member with respect to the first registration member with the pivot axis as a fulcrum to change the relative postures.

6. The osteotomy assistance jig according to claim 5, wherein:

the coupling member is configured to be capable of extending and contracting a coupling length of the coupling member, and the coupling length is associated with a rotation angle of the second registration member with respect to the first registration member.

7. The osteotomy assistance jig according to claim 1, further comprising a reference antenna disposed in the first registration member and for defining a position of the osteotomy assistance jig in a superior-inferior direction.

8. The osteotomy assistance jig according to claim 7, wherein the position of the osteotomy assistance jig in the superior-inferior direction is variable, the position being defined by the reference antenna.

9. The osteotomy assistance jig according to claim 1, further comprising an angle detection section that detects a rotation angle when the second registration member rotates with respect to the first registration member with the pivot axis as a fulcrum.

10. The osteotomy assistance jig according to claim 1, wherein:

the first registration member includes a distal screw bolt guide section for setting the fixing position of the distal screw bolt, and at least relative positions of the distal screw bolt guide section and the pivot axis and/or relative postures of the distal screw bolt guide section and the pivot axis are variable.

11. The osteotomy assistance jig according to claim 10, wherein:

the first registration member includes a rotation axis setting plate that sets or fixes the pivot axis, the distal screw bolt guide section is formed in the positioning plate, and at least relative positions and/or relative postures between the positioning plate and the rotation axis setting plate are variable.

12. The osteotomy assistance jig according to claim 11, wherein:

the first registration member includes a coupling arm that couples the positioning plate to the rotation axis setting plate, and the coupling arm has a variable length.

13. The osteotomy assistance jig according to claim 12, wherein the coupling arm is configured to be interchangeable with respect to the positioning plate and the rotation axis setting plate, and is selected from a plurality of variations having different lengths.

14. The osteotomy assistance jig according to claim 10, wherein:

the first registration member includes a rotation axis setting plate that sets or fixes the pivot axis, the distal screw bolt guide section is formed in the positioning plate, and the first registration member is selected from a plurality of variations in which at least relative positions of the positioning plate and the rotation axis setting plate and/or relative postures of the positioning plate and the rotation axis setting plate differ.

15. A digital template in which the osteotomy assistance jig according to claim 1 is modeled in a side view, the digital template to be drawn comprising:

registration information indicating a position and a posture of the osteotomy assistance jig;

bone cutting surface information indicating a bone cutting surface associated with the osteotomy assistance jig;

candidate position information on the pivot axis;

fixing position information on the distal screw bolt; and fixing position information on the proximal screw bolt.

16. The digital template according to claim 15, wherein the digital template includes fixing plate information in which the fixing plate is modeled in a side view.

17. A long bone corrective osteotomy which is performed by using the osteotomy assistance jig of claim 1, the long bone corrective osteotomy comprising:

performing preoperative planning by using the digital template according to claim 15;

adjusting the connection position and the connection angle of the second registration member with respect to the first registration member according to the preoperative planning;

installing the osteotomy assistance jig in a predetermined portion of the long bone according to the preoperative planning;

inserting a guide pin into the fixing position of the distal screw bolt and the fixing position of the proximal screw bolt by using the osteotomy assistance jig, before cutting the long bone;

performing bone cutting of the long bone;

positioning the fixing plate by using the guide pin as a guide while rotating the long bone after the bone cutting; and inserting the distal screw bolt and the proximal screw bolt along the guide pin to fix the fixing plate to the long bone.

* * * * *